United States Patent [19]

Urbahns et al.

[11] Patent Number: 5,756,515
[45] Date of Patent: May 26, 1998

[54] DIOXO-THIOPYRANO-PYRIDINE-CARBOXYLIC ACID DERIVATIVES AND THEIR USE AS MEDICAMENTS

[75] Inventors: Klaus Urbahns, Wuppertal; Hans-Georg Heine, Krefeld; Bodo Junge; Rudolf Schohe-Loop, both of Wuppertal; Henning Sommermeyer, Köln; Thomas Glaser, Overath; Reilinde Wittka, Köln; Jean-Marie-Viktor de Vry, Rösrath, all of Germany

[73] Assignee: Bayer Aktiengesellschaft, Leverkusen, Germany

[21] Appl. No.: 776,215

[22] PCT Filed: Jun. 30, 1995

[86] PCT No.: PCT/EP95/02546

§ 371 Date: Jan. 6, 1997

§ 102(e) Date: Jan. 6, 1997

[87] PCT Pub. No.: WO96/02547

PCT Pub. Date: Feb. 1, 1996

[30] Foreign Application Priority Data

Jul. 13, 1994 [DE] Germany .................. 44 24 678.1

[51] Int. Cl.$^6$ .................. A61K 31/44; C07D 495/04
[52] U.S. Cl. .................. 514/301; 546/114
[58] Field of Search .................. 546/114; 514/301

[56] References Cited

U.S. PATENT DOCUMENTS 4,705,785  11/1987  Schwender et al. .................. 514/211

OTHER PUBLICATIONS

P.W.L. Tas, et al., Neuroscience Letters, vol. 94, pp. 279–284 (1985).
J. Dodd, J. Het. Chem., vol. 27, No. 5, pp. 1453–1456 (1990).

*Primary Examiner*—Patricia L. Morris
*Attorney, Agent, or Firm*—Sprung Kramer Schaefer & Briscoe

[57] ABSTRACT

Dioxo-thiopyrano-pyridine-carboxylic acid derivatives are prepared by reacting appropriate aldehydes with aminocrotonic acid esters and tetrahydrothiopyran-3-one-1.1-dioxide and oxidizing the products thus obtained. The substances according to the invention can be employed as active substances in medicaments. They are selective modulators of the calcium-dependent potassium channels of high conductivity.

6 Claims, No Drawings

DIOXO-THIOPYRANO-PYRIDINE-CARBOXYLIC ACID DERIVATIVES AND THEIR USE AS MEDICAMENTS

The present invention relates to dioxo-thiopyrano-pyridine-carboxylic acid derivatives, a process for their preparation and their use as medicaments, in particular as cerebrally active agents.

Cyclic sulphone dihydropyridines are already known [cf. J. Heterocycl. Chem. 27 (5), 1453–6, 1990].

The present invention relates to new 1,1-dioxo-2H-thiopyrano-[2,3-b]pyridine-7-carboxylic acid derivatives and esters of the general formula (I)

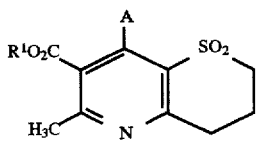
(I)

in which
- A represents aryl having 6 to 10 carbon atoms, or pyridyl, each of which is optionally substituted up to 3 times by identical or different substituents from the group consisting of nitro, cyano, cycloalkyl having 3 to 7 carbon atoms, halogen and trifluoromethyl or by straight-chain or branched alkylthio, alkyl or alkoxy in each case having up to 6 carbon atoms,
- $R^1$ represents hydrogen or straight-chain or branched alkyl having up to 8 carbon atoms, and their salts.

In the context of the invention, physiologically acceptable salts are preferred. In general, physiologically acceptable salts are salts of the compounds according to the invention with inorganic or organic acids. Salts with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid are preferred.

The compounds according to the invention can exist in stereoisomeric forms which behave either as image and mirror image (enantiomers) or which do not behave as image and mirror image (diastereomers). The invention relates both to the antipodes and to the racemic forms as well as the diastereomer mixtures. Like the diastereomers, the racemic forms can be separated into the stereoisomerically homogeneous constituents in a known manner.

Preferred compounds of the general formula (I) are those in which
- A represents phenyl, naphthyl or pyridyl, each of which is optionally substituted up to 3 times by identical or different substituents from the group consisting of nitro, cyano, fluorine, chlorine, bromine, iodine, cyclopropyl, cyclopentyl, cyclohexyl and trifluoromethyl or by straight-chain or branched alkylthio, alkyl or alkoxy in each case having up to 4 carbon atoms,
- $R^1$ represents hydrogen or straight-chain or branched alkyl having up to 6 carbon atoms, and their salts.

Particularly preferred compounds of the general formula (I) are those
in which
- A represents phenyl or pyridyl, each of which is optionally substituted up to 3 times by identical or different substituents from the group consisting of nitro, cyano, fluorine, chlorine, bromine, iodine, trifluoromethyl, cyclohexyl, methyl and methoxy or by methylthio,
- $R^1$ represents hydrogen or straight-chain or branched alkyl having up to 4 carbon atoms, and their salts.

A process for the preparation of the compounds of the general formula (I) according to the invention has additionally been found, characterized in that aldehydes of the general formula (II)

(II)

in which
A has the abovementioned meaning,
are reacted with compounds of the general formula (III)

(III)

in which
$R^3$ has the abovementioned meaning of $R^1$, but does not represent hydrogen, and tetrahydrothiopyran-3-one-1,1-dioxide,
in inert solvents first to give the compounds of the general formula (IV)

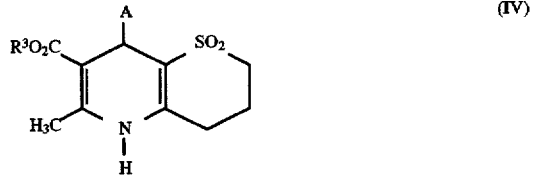
(IV)

in which
A and $R^3$ have the abovementioned meaning,
and in a second step an oxidation is carried out in inert solvents,
and in the case of the acids ($R^1$=H) the esters are hydrolysed.

The process according to the invention can be illustrated by way of example by the following reaction scheme:

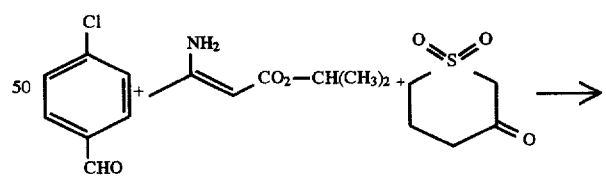

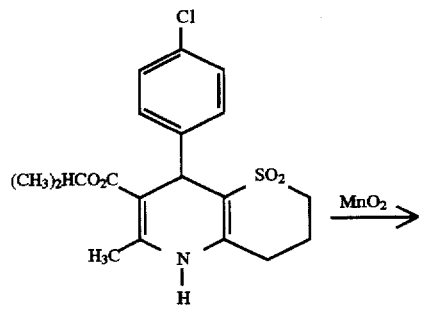

-continued

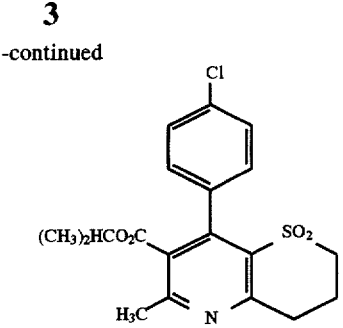

Suitable solvents in this connection are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether, acetonitrile, or amides such as hexamethylphosphoramide or dimethylformamide, or acetic acid or halogenated hydrocarbons such as methylene chloride or carbon tetrachloride or hydrocarbons such as benzene or toluene. It is also possible to use mixtures of the solvents mentioned. Ethanol is preferred.

The reaction temperatures can be varied within a relatively wide range. In general, the reaction is carried out between +10° C. and +150° C., preferably between +20° C. and +100 C., in particular at the boiling point of the particular solvent.

The reactions can be carried out at normal pressure, but also at elevated or reduced pressure (e.g. 0.5 to 3 bar). In general the reactions are carried out at normal pressure.

Suitable solvents for the oxidation are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether, acetonitrile, or amides such as hexamethylphosphoramide or dimethylformamide, or acetic acid or halogenated hydrocarbons such as methylene chloride or carbon tetrachloride or hydrocarbons such as benzene or toluene. It is also possible to use mixtures of the solvents mentioned. Methylene chloride is preferred.

In general, suitable oxidizing agents are 2,3-dichloro-4, 5-dicyano-p-benzoquinone and derivatives, pyridinium dichromate, elemental bromine or iodine and manganese dioxide. Manganese dioxide is preferred.

In general, the oxidizing agent is employed in an amount from 1 mol to 20 mol, preferably from 1 mol to 5 mol, relative to 1 mol of the compounds of the general formula (IV).

The reaction temperatures can be varied within a relatively wide range. In general, the reaction is carried out between +10° C. and +150° C., preferably between +20° C. and +100° C., in particular in the boiling range of the solvent used.

The reactions can be carried out at normal pressure, but also at elevated or reduced pressure (e.g. 0.5 to 3 bar). In general, the reactions are carried out at normal pressure.

The hydrolysis of the carboxylic acid esters is carried out according to customary methods, by treating the esters with customary bases in inert solvents.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate. Sodium hydroxide or potassium hydroxide is particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

In general, the hydrolysis is carried out in a temperature range from 0° C. to +100° C., preferably from +20° C. to +80° C.

The hydrolysis is in general carried out at normal pressure. However, it is also possible to work at reduced pressure or at elevated pressure (e.g. from 0.5 to 5 bar).

Enantiomerically pure forms are obtained e.g. by separating diastereomer mixtures of the compounds of the general formula (I), in which $R^1$ represents an optically active ester radical, according to a customary method, then either transesterifying directly or first preparing the chiral carboxylic acids and then preparing the enantiomerically pure compounds by esterification.

The separation of the diastereomers is in general carried out either by fractional crystallization, by column chromatography or by countercurrent distribution. Which is the optimum process must be decided from case to case, sometimes it is also expedient to use combinations of the individual processes. Separation by crystallization or countercurrent distribution or a combination of both processes is particularly suitable.

The enantiomerically pure compounds are also accessible by chromatography of the racemic esters on chiral phases.

The compounds of the general formulae (II) and (III) are known per se.

The compounds of the general formula (IV) are known in some cases or can be prepared, for example, as described above.

The compounds of the general formula (I) according to the invention show an unforeseeable, useful spectrum of pharmacological action.

They are modulators with selectivity for calcium-dependent potassium channels of high conductivity (BK(Ca) channels), in particular of the central nervous system.

On account of their pharmacological properties, they can be used for the production of medicaments for the treatment of degenerative central nervous system disorders, such as dementias, for example multi-infarct dementia (MID), primary degenerative dementia (PDD), pre-senile and senile dementia of the Alzheimer's disease type, HIV dementia and other forms of dementia, Parkinson's disease or amyotrophic lateral sclerosis and also multiple sclerosis.

The active compounds are furthermore suitable for the treatment of brain function disorders in old age, of organic brain syndrome (OBS) and of age-related memory disorders (age-associated memory impairment, AAMI).

They are suitable for the prophylaxis and treatment of the sequelae of cerebral circulatory disorders such as cerebral ischaemias, strokes, craniocerebral traumata and subarachnoid haemorrhages.

They are useful for the treatment of depressions and psychoses, e.g. schizophrenia. They are additionally suitable for the treatment of disorders of neuroendocrine secretion and of neurotransmitter secretion and health disorders connected therewith such as mania, alcoholism, drug abuse, dependence or abnormal eating behaviour. Other application areas are the treatment of migraine, of sleep disorders and of neuropathies. They are moreover suitable as analgesics.

The active compounds are furthermore suitable for the treatment of disorders of the immune system, in particular of T-lymphocyte proliferation and for affecting the smooth musculature, in particular of uterus, urinary bladder and bronchial tract and for the treatment of diseases connected therewith such as e.g. asthma and urinary incontinence and for the treatment of high blood pressure, arrhythmia, angina and diabetes.

$^{86}$Rubidium Efflux from C6-BU1 Glioma Cells

The experiments were carried out with slight changes according to the method described by Tas et al. (Neurosci Lett. 94, 279–284, (1988)). For this, rat C6-BU1 glioma cells are cultured in 24-well culture dishes; on the day of the experiment the culture medium is removed, and the cells are thoroughly washed with incubation medium, consisting of HEPES-buffered saline solution (HBS, HEPES 20 mM, NaCl 150, KCl 5.4, CaCl$_2$ 1.8, MgCl$_2$ 0.8, NaHPO$_4$ 0.84, glucose 5.5). The cells are then loaded with $^{86}$Rubidium ($^{86}$Rb, 0.25 µCi/well) in incubation medium for 60 min. After filtering off the $^{86}$Rb solution with suction and washing the cells, 1 µM ionomycin in the absence and presence of test substance is pipetted in in incubation buffer (total volume 0.5 ml) to stimulate $^{86}$Rb efflux and the mixture is incubated at 37° C. for 10 min. For the determination of the efflux, the supernatant is transferred to counting vials. For the determination of the intracellular $^{86}$Rb still remaining, the cells are treated with 0.5M NaOH/0.1% Triton X 100 for 30 min. The solution is then transferred to counting vials. The amount of $^{86}$Rb contained in the counting vials is determined in a liquid scintillation counter. The increase in the efflux above the basal efflux produced by ionomycin is calculated from the data and set to 100%. The stimulations in the presence of test substances are then based on this value.

The present invention also includes pharmaceutical preparations which, in addition to inert, non-toxic, pharmaceutically suitable auxiliaries and excipients, contain one or more compounds of the general formula (I), or which consist of one or more active substances of the formula (I), and processes for the production of these preparations.

The active substances of the Formula (I) should be present in these preparations in a concentration of from 0.1 to 99.5% by weight, preferably from 0.5 to 95% by weight of the total mixture.

In addition to the active substances of the Formula (I) the pharmaceutical preparations can also contain other pharmaceutical active substances.

The abovementioned pharmaceutical preparations can he prepared in a customary manner according to known methods, for example using the auxiliary(ies) or excipient (s).

In general, it has proven advantageous to administer the active substance(s) of the formula (I) in total amounts of from approximately 0.01 to approximately 100 mg/kg, preferably in total amounts of from approximately 1 mg/kg to 50 mg/kg of body weight every 24 hours, if appropriate in the form of several individual doses, to achieve the desired result.

However, it may in some cases be advantageous to deviate from the amounts mentioned, namely depending on the species and the body weight of the subject treated, on individual behaviour to the medicament, the nature and severity of the disorder, the type of preparation and administration, and the time or interval at which administration takes place.

Eluent Mixtures:

| | |
|---|---|
| a | Methylene chloride/AcOH 10 + 1 |
| b | Methylene chloride/MeOH 10 + 1 |
| c | PE/AcOEt 7 + 3 |
| d | PE/AcOEt 1 + 1 |

Starting Compounds

EXAMPLE I

Isopropyl 3,4,5,8-tetrahydro-8-(4-chlorophenyl)-1,1-dioxo-2H-thiopyrano[2,3 b]-pyridine-7-carboxylate

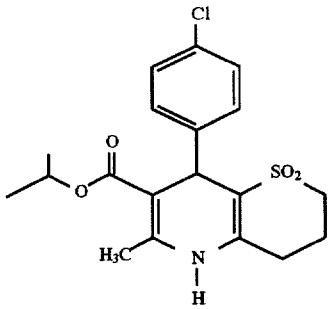

2.40 g (20 mmol) of 4-chlorobenzaldehyde, 4.86 g (20 mmol) of isopropyl aminocrotonate and 2.96 g (20 mmol) of tetrahydrothiopyran-3-one-1,1-dioxide are boiled under reflux for 3 h in ethanol. The solid which is deposited is filtered off with suction and washed with ethanol (5 g, 63%).

Preparation Examples

EXAMPLE 1

Isopropyl 3,4-dihydro-8-(4-chlorophenyl)-1,1-dioxo-2H-thiopyrano-[2,3-b]-pyridine-7-carboxylate

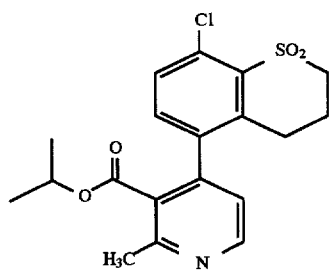

2.0 g (5.0 mmol) of the compound from Example I are dissolved in 150 ml of CH$_2$Cl$_2$ and treated with 7.0 g of MnO$_2$. The mixture is kept under reflux for 2 h, filtered off with suction through Celite and concentrated. The residue crystallizes from ether/petroleum ether. 1.77 g (90%) are obtained, (MS: 393), R$_f$ (b) 0.86.

The compounds listed in Table I are prepared in analogy to the procedure of Example 1:

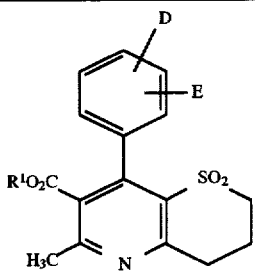

| Ex. No. | R¹ | D | E | $R_f°$ | Yield (% of theory) |
|---|---|---|---|---|---|
| 2 | —CH₃ | 4-Cl | 3-H | 0.73 (b) | 77 |
| 3 | —CH₃ | 2-Cl | 3-Cl | 0.79 (b) | 68 |
| 4 | —CH(CH₃)₂ | 2-Cl | 3-Cl | 0.71 (b) | 87 |

We claim:

1. A dioxo-thiopyrano-pyridine-carboxylic acid derivative of the formula

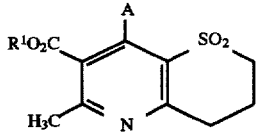

(I)

in which
- A represents aryl having 6 to 10 carbon atoms, or pyridyl, each of which is optionally substituted up to 3 times by identical or different substituents from the group consisting of nitro, cyano, cycloalkyl having 3 to 7 carbon atoms, halogen and trifluoromethyl or by straight-chain or branched alkylthio, alkyl or alkoxy in each case having up to 6 carbon atoms,
- R¹ represents hydrogen or straight-chain or branched alkyl having up to 8 carbon atoms, or a salt thereof.

2. A dioxo-thiopyrano-pyridine-carboxylic acid derivative according to claim 1
where
- A represents phenyl, naphthyl or pyridyl, each of which is optionally substituted up to 3 times by identical or different substituents from the group consisting of nitro, cyano, fluorine, chlorine, bromine, iodine, trifluoromethyl, cyclopropyl, cyclopentyl and cyclohexyl or by straight-chain or branched alkylthio, alkyl or alkoxy in each case having up to 4 carbon atoms,
- R¹ represents hydrogen or straight-chain or branched alkyl having up to 6 carbon atoms, or a salt thereof.

3. A dioxo-thiopyrano-pyridine-carboxylic acid derivative according to claim 1,
in which
- A represents phenyl or pyridyl, each of which is optionally substituted up to 3 times by identical or different substituents from the group consisting of nitro, cyano, fluorine, chlorine, bromine, iodine, trifluoromethyl, cyclohexyl, methyl and methoxy or by methylthio,
- R¹ represents hydrogen or straight-chain or branched alkyl having up to 4 carbon atoms, or a salt thereof.

4. A process for the preparation of a dioxo-thiopyrano=pyridine-carboxylic acid derivative according to claim 1 which comprises:

1. reacting an aldehyde of the formula

A—CHO  (II)

in which A has the above-mentioned meaning, with a compound of the formula

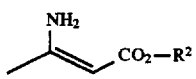

(III)

in which
R² has the above-mentioned meaning of R¹, but does not represent hydrogen, and with tetrahydrothiopyran-3-one-1,1-dioxide, in an inert solvent first to give a compound of the formula

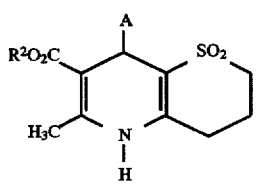

(IV)

in which
A and R² have the abovementioned meaning, and 2. oxidizing the compound formed in the step above with an oxidizing agent selected from the group consisting of 2,3-dichloro-4,5-dicyano-p-benzoquinone, pyridinium dichromate, elemental bromine, elemental iodine and maganese dioxide in an inert solvent and in the case wherein the final product is an acid (R¹ is H), performing a hydrolysis step to remove the ester.

5. The process according to claim 4, wherein the oxidizing agent is manganese dioxide.

6. A pharmaceutical composition which comprises a dioxo-thiopyrano-pyridine-carboxylic acid derivative according to claim 1 and a pharmaceutically acceptable auxiliary or excipient.

* * * * *